United States Patent
Swauger

Patent Number: 5,413,562
Date of Patent: May 9, 1995

[54] STABILIZING FITTING FOR AN INTRAVENOUS CATHETER OR SYRINGE

[76] Inventor: Jonathan L. Swauger, 28163 Tambora Dr., Canyon Country, Calif. 91351

[21] Appl. No.: 261,732
[22] Filed: Jun. 17, 1994
[51] Int. Cl.⁶ ............................................. A61M 25/02
[52] U.S. Cl. ......................... 604/179; 128/DIG. 26; 604/174
[58] Field of Search ............... 604/174, 179, 177; 128/DIG. 26

[56] References Cited

U.S. PATENT DOCUMENTS

| | | | |
|---|---|---|---|
| 3,059,645 | 10/1962 | Hasbrouck et al. | 604/179 |
| 3,630,195 | 12/1971 | Santomieri . | |
| 3,696,920 | 10/1972 | Lahay . | |
| 3,812,851 | 5/1974 | Rodriguez . | |
| 3,826,254 | 7/1974 | Mellor . | |
| 3,834,380 | 9/1974 | Boyd . | |
| 4,027,668 | 6/1977 | Dunn . | |
| 4,129,128 | 12/1978 | McFarlane . | |
| 4,165,748 | 8/1979 | Johnson . | |
| 4,224,937 | 9/1980 | Gordon . | |
| 4,250,880 | 2/1981 | Gordon . | |
| 4,316,461 | 2/1982 | Marais et al. . | |
| 4,333,468 | 6/1982 | Geist . | |
| 4,380,234 | 4/1983 | Kamen . | |
| 4,449,975 | 5/1984 | Perry . | |
| 4,484,913 | 11/1984 | Swauger . | |
| 4,563,177 | 1/1986 | Kamen | 128/DIG. 26 |
| 4,669,458 | 6/1987 | Abraham et al. . | |
| 4,702,736 | 10/1987 | Kalt et al. . | |
| 4,737,143 | 4/1988 | Russell | 128/DIG. 26 |
| 4,846,807 | 7/1989 | Safadaco | 604/179 |
| 4,898,587 | 2/1990 | Mera . | |
| 5,084,026 | 1/1992 | Shapiro | 604/179 |
| 5,263,943 | 11/1993 | Vanderbrook | 604/179 |
| 5,334,186 | 8/1994 | Alexander | 604/179 |
| 5,336,195 | 8/1994 | Daneshuar | 604/179 |

Primary Examiner—Paul J. Hirsch
Attorney, Agent, or Firm—Kelly, Bauersfeld & Lowry

[57] ABSTRACT

A stabilizing fitting useful for securing a catheter hub or a syringe body adjacent to a venipuncture site is provided. The stabilizing fitting, of unitary pliable plastic construction, includes an elongated base having support members at each end. A VELCRO fastener is secured to an upper surface of each support member. A retaining strap removably attachable to the VELCRO fastener may be looped about the patient's arm, for example, to secure the stabilizing fitting in place without the use of skin-contacting adhesives. A catheter hub/syringe body retainer is centrally disposed between the support members and surrounded by a catheter hub/syringe body wing housing. A plurality of medical tube retaining slots are provided through each support member in alignment with the catheter hub/syringe body retainer. A lower surface of the base includes recesses for the retainer, the wing housing and the medical tube retaining slots.

25 Claims, 1 Drawing Sheet

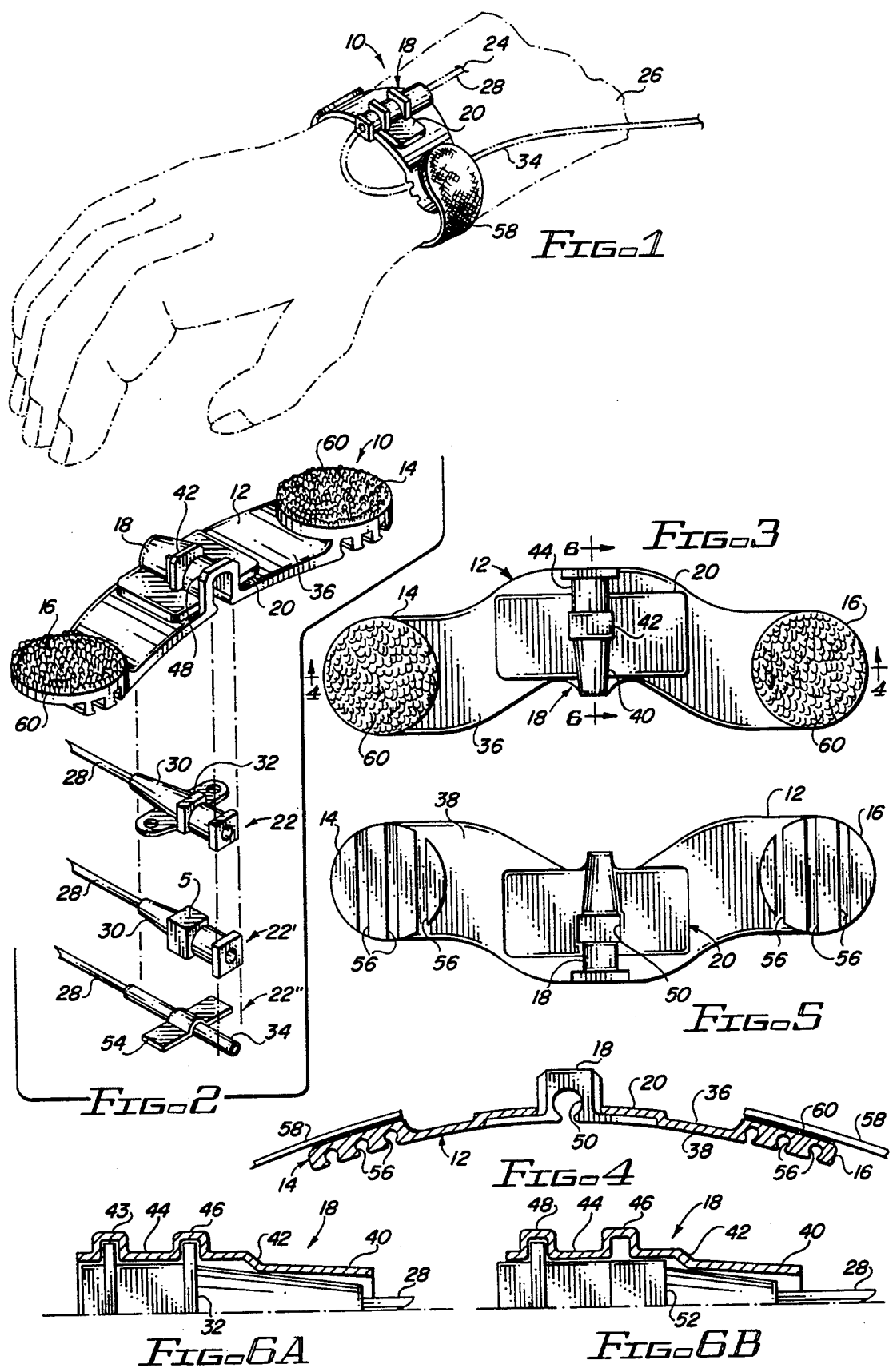

STABILIZING FITTING FOR AN INTRAVENOUS CATHETER OR SYRINGE

BACKGROUND OF THE INVENTION

This invention relates generally to a medical apparatus for fastening a tube to a part of a body. More specifically, this invention relates to a stabilizing fitting for securing a catheter hub or a syringe body adjacent to a venipuncture site.

Many intravenous lines are placed into patient's daily. A venipuncture can be made in many areas of the body, such as the forearm, back of the hand, upper arm, ankle or foot. In a typical procedure, a catheter is normally inserted into a vein by means of a hollow needle which is then withdrawn to avoid damage to the walls of the punctured vein. The catheter remains attached to the patient and is connected to a source of infusion liquid. It is then necessary to stabilize the catheter to prevent movement which may work the catheter loose and create a potential source of infection or irritation to the patient at the point of catheter insertion. This stabilization is generally done by taping the catheter hub and associated tube fittings to the patient's skin in an area adjacent to the point of catheter insertion.

It is also conventional practice to insert the needle of a syringe into a vein of a patient undergoing medical treatment, and the syringe as well as its attendant fluid feeding tubes are retained on the limb by adhesive tape which is wrapped about the syringe, tubing and the limb of the patient. It is also routine practice to check fluid flow through the syringe by replacing the tubing periodically since collapse of the tubing is sometimes encountered when the fluid introduced to the patient by the syringe has been exhausted. During such a checking procedure, the tubing is removed from the syringe, which sometimes causes the syringe needle to be inadvertently withdrawn from its insertion into the vein of the patient. Obviously, such a procedure is cumbersome and awkward, as well as painful and inconvenient to the patient, especially when reinsertion of the syringe needle is required.

Although it is important to obtain secure stabilization of the inserted catheter or needle, many medical personnel do not have the skill to make a proper stabilizer utilizing ordinary hospital self-adhesive tape. Even when the medical personnel have sufficient skill, such use of adhesive tape is not always desirable. For example, repeated application and removal of adhesive tape from the skin of a long-term patient may damage the skin of the patient and be quite painful.

Accordingly, there has been a need for a novel stabilizing fitting which is useful for securing a catheter hub or a syringe body adjacent to a venipuncture site. Such a stabilizing fitting should be of simplified construction, inexpensive to manufacture, and easy to be understood and used by medical personnel. Additionally, a device is needed which may be readily attached to or detached from the patient without the use of adhesives, and which may be disposed of after use. Moreover, a need exists for such a stabilizing fitting which is easy to place upon the limb of the patient, and is adapted to hold not only the catheter hub or syringe body, but also the tubes feeding fluid to the venipuncture site as well. The present invention fulfills these needs and provides other related advantages.

SUMMARY OF THE INVENTION

The present invention resides in a stabilizing fitting for an intravenous catheter or syringe, which is compact, easy to manufacture, and which may be secured adjacent to a venipuncture site without the use of adhesives or an adhesive tape. The stabilizing fitting comprises, generally, an elongated base having a first support member at a first end thereof, and a second support member at a second end thereof. A catheter hub/syringe body retainer is centrally disposed between the first and second support members. Additionally, a catheter hub/syringe body wing housing is centrally disposed between the first and second support members, and surrounds a portion of the catheter hub/syringe body retainer.

In a preferred form of the invention, a plurality of medical tube retaining slots are provided through the first and second support members. The medical tube retaining slots are aligned parallel with a longitudinal axis of the catheter hub/syringe body retainer. Means fixed to an upper surface of the base are provided for attaching the stabilizing fitting to a retaining strap. The attaching means include VELCRO fasteners secured to the first and second support members.

The longitudinal axis of the catheter hub/syringe body retainer extends generally perpendicular to a longitudinal axis of the base. The catheter hub/syringe body retainer includes a frusto-conical first portion extending from one end thereof to a shoulder. A generally cylindrical second portion extends from another end thereof to the shoulder, and a pair of spaced-apart projections extend radially outwardly from the second portion of the retainer.

A lower surface of the base includes recesses for the catheter hub/syringe body retainer, the wing housing, and the medical tube retaining slots.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view of a stabilizing fitting for an intravenous catheter or syringe embodying the invention, illustrating the use of the stabilizing fitting to secure a catheter hub or a syringe body adjacent to a venipuncture site on the arm of a patient, utilizing a retaining strap;

FIG. 2 is an enlarged perspective view of the stabilizing fitting shown in FIG. 1, illustrating several different types of syringes that may be advantageously utilized in connection therewith;

FIG. 3 is an enlarged top plan view of the stabilizing fitting shown in FIGS. 1 and 2;

FIG. 4 is a sectional view taken generally along the line 4—4 of FIG. 3;

FIG. 5 is a bottom plan view of the stabilizing fitting shown in FIGS. 1-4;

FIG. 6A is an enlarged sectional view taken generally along the line 6—6 of FIG. 4, illustrating the construction of a catheter hub/syringe body retainer and showing the positioning of one type of syringe body therein; and FIG. 6B is a view similar to FIG. 6A, showing the positioning of another type of syringe body within the retainer.

DETAILED DESCRIPTION OF THE PREFERRED EMBODIMENT

As shown in the drawings for purposes of illustration, the present invention is concerned with an improved stabilizing fitting for an intravenous catheter or syringe, generally designated in the accompanying drawings by the reference number 10. The stabilizing fitting 10 comprises, generally, an elongated base 12 having a first support member 14 at a first end thereof, and a second support member 16 at a second end thereof. A catheter hub/syringe body retainer 18 is centrally disposed between the first and second support members 14 and 16. Additionally, a catheter hub/syringe body wing housing 20 is centrally disposed between the first and second support members 14 and 16, and surrounds a portion of the retainer 18. The stabilizing fitting 10 is useful for securing a catheter hub or a syringe body 22 adjacent to a venipuncture site 24, illustrated in FIG. 1 on the forearm 26 of a patient.

With reference to FIG. 2, several syringe bodies 22 which may be advantageously secured adjacent to the venipuncture site 24 utilizing the stabilizing fitting 10 are shown by way of example only. A shaped syringe body of one configuration is indicated by the number 22, while another configuration is indicated by the number 22'. Additionally, a "butterfly" syringe body is indicated by the number 22''. In each case a needle 28 is carried by each syringe body 22-22'' at its forward end, which is inserted through the skin of the patient into an appropriate vein. The syringe bodies 22 and 22' further include a coupling element 30 which includes an enlarged semi-encircling flange 32. As is the conventional practice, the coupling element 30 is inserted into the rear end of the respective syringe body as illustrated, and its opposite end is attached to one end of a fluid carrying medical tube 34 The syringes 22-22' the needles 28, the coupling elements 30 and the medical tubes 34 are conventional and do not, in themselves, form the present invention. They are illustrated by way of example to show the various types of syringe bodies that may be used advantageously with the stabilizing fitting 10 of the present invention.

Although several different types of syringe bodies 22-22'' have been illustrated for use in connection with the stabilizing fitting 10, the stabilizing fitting 10 is also advantageously utilized in connection with a standard catheter hub (not shown). By way of background, when it is desired that a flexible catheter be inserted into the vein of a patient, a venipuncture is made in the normal way utilizing a needle which extends coaxially with the end of the catheter to be inserted into the vein. After the venipuncture is made, the needle is withdrawn from the catheter and after checking the blood flashback, the catheter hub is connected to its associated infusion tube fittings. It is often desirable to secure the catheter hub, together with the adjacent medical tube fittings, adjacent to the venipuncture site without utilizing adhesive tape or other forms of adhesive in contact with the skin of the patient.

In accordance with the present invention, the elongated base 12 has an upper surface 36, a lower surface 38 and, as mentioned previously, first and second support members 14 and 16 disposed at opposite ends thereof. A catheter hub/syringe body retainer 18 is centrally disposed between the first and second support members 14 and 16 such that a longitudinal axis of the retainer 18 extends generally perpendicular to a longitudinal axis of the base 12. The retainer 18 includes a frusto-conical first portion 40 which extends from one end of the retainer 18 to a shoulder 42, and a generally cylindrical second portion 44 which extends from another end of the retainer to the shoulder 42. The retainer 18 further includes a pair of spaced-apart hollow projections 46 and 48 which extend radially outwardly from the second portion 44.

Either syringe body 22 or 22' may be captured within a recess 50 in the lower surface 38 of the base 12 formed by the retainer 18, so that the syringe is forcibly urged against the skin of the patient's limb and, therefore, held in place. With reference to FIG. 6A, the retainer 18 holds or retains the syringe body 22 in position since the flange 32 carried on the body thereof is captured within the recess of the projection 46. The forward portion of the syringe body 22 constituting the coupling element 30 is captured beneath the frusto-conical first portion 40 of the retainer 18. With reference to FIG. 6B, it will be noted that the syringe body 22' is captured within the same recess 50 of the retainer 18 wherein a square 52 of the syringe body is captured by the shoulder 42, and the flange 32 is captured within the recess or hollow of the second projection 48.

In order to accommodate the syringe body 22'', the base 12 further includes a catheter hub/syringe body wing housing 20 which is centrally disposed between the first and second support members 14 and 16, and which surrounds a portion of the retainer 18. The wing housing 20 is adapted, particularly, to receive the wings 54 of a butterfly syringe, illustrated at 22''.

Three medical tube retaining slots 56 are provided through each support member 14 and 16. These retaining slots 56 run parallel to the longitudinal axis of the retainer 18, and define recesses in the lower surface 38 of the base 12. The base 12 is preferably of a one piece or unitary construction of pliable plastic material which permits components of the stabilizing fitting 10 to be resiliently deformed temporarily for placement, for example, of a portion of the fluid carrying medical tube 34 through a selected slot 56. The location of the retaining slots 56 at opposite distal ends of the base 12 relative to the retainer 18 permits medical tubes 34 to be placed within and removed from the retaining slots 56 without disturbing the syringe body or catheter hub at the venipuncture site 24.

Means are fixed to the upper surface 36 of the base 12 over the support members 14 and 16, for attaching the stabilizing fitting 10 to a retaining strap 58. The attaching means comprise a VELCRO fastener 60 in the form of hook tape which is secured to the base 12 immediately above the retaining slots 56. The retaining strap 58 preferably includes end sections having a pile construction which may be gripped by the hook tape VELCRO fastener 60 of the stabilizing fitting 10. Thus, after the stabilizing fitting 10 is properly placed adjacent to the venipuncture site 24, the retaining strap 58 may be attached to one of the support members 14, looped around the limb of the patient and then attached to the other support member to secure the stabilizing fitting 10 in place without the use of skin-contacting adhesives.

From the foregoing it is to be appreciated that the improved stabilizing fitting 10 for an intravenous catheter or syringe is quite easy to use by medical personnel, may be manufactured efficiently and economically and thus disposed of after use, and eliminates the need for skin-contacting adhesive adjacent to the venipuncture site 24 for the purpose of holding a syringe body or catheter hub in place. In actual use, the needle 28 is inserted through the skin of the patient and, in the case that the needle 28 will be left within the vein, the syringe body is placed within the retainer 18, or in the case of a catheter, the needle 28 is removed and the catheter hub and associated medical tubing elements are placed within the retainer 18 as the stabilizing fitting 10 is placed against the skin of the patient. If a butterfly syringe 22″ is utilized, the wings 54 thereof are easily received within the wing housing 20 which surrounds the retainer 18. The medical tubing 34 extending away from the venipuncture site 24 may be secured within one or more of the retaining slots 56, and then the retaining strap 58 may be attached to the VELCRO fasteners 60 over the first and second support members 14 and 16 in order to secure the stabilizing fitting 10 to the patient.

The support members 14 and 16 protect the user from inflammation or other discomfort caused by tape or the like, and no preparation is required on the skin of the user such as shaving, etc., which is common when adhesive tape is utilized. In order to change the tubing 34, the coupling element 30 may readily be removed from the backside of the syringe body 22 while the needle 28 still extend s through the skin of the patient. The stabilizing fitting 10 stabilizes and the syringe and by gentle manipulation the attendant can hold the syringe and pull the coupling element 30 therefrom. When the injection is no longer required, the needle, syringe, tubing and the fitting 10 may readily be discarded as a single unit.

Although a particular embodiment of the invention has been described in detail for purposes of illustration, various modifications may be made without departing from the spirit and scope of the invention. Accordingly, the invention is not to be limited, except as by the appended claims.

I claim:

1. A stabilizing fitting for an intravenous catheter or syringe, comprising:
   an elongated base having a first support member at a first end thereof, and a second support member at a second end thereof;
   a catheter hub/syringe body retainer disposed between the first and second support members; and
   a catheter hub/syringe body wing housing centrally disposed between the first and second' support members, and surrounding a portion of the catheter hub/syringe body retainer.

2. The stabilizing fitting of claim 1, wherein the base has an upper surface including means for attaching the stabilizing fitting to a retaining strap, and a lower surface including recesses for the catheter hub/syringe body retainer and the wing housing.

3. The stabilizing fitting of claim 2, including a medical tube receiving slot through at least one of the first or second support members.

4. The stabilizing fitting of claim 3, wherein the base lower surface includes a recess for the medical tube receiving slot.

5. The stabilizing fitting of claim 2, including a plurality of medical tube receiving slots through at least one of the first or second support members, wherein the base lower surface includes a corresponding plurality of recesses for the medical tube receiving slots.

6. The stabilizing fitting of claim 2, wherein the recess for the catheter hub/syringe body retainer extends generally perpendicular to a longitudinal axis of the base.

7. The stabilizing fitting of claim 6, including a plurality of medical tube receiving slots through at least one of the first or second support members, wherein the base lower surface includes a corresponding plurality of recesses for the medical tube receiving slots, and wherein the recesses of the medical tube receiving slots run parallel to the recess for the catheter hub/syringe body retainer.

8. The stabilizing fitting of claim 1, wherein the catheter hub/syringe body retainer includes a frusto-conical first portion extending from one end thereof to a shoulder, a generally cylindrical second portion extending from another end thereof to the shoulder, and a pair of spaced-apart projections extending radially outwardly from the second portion.

9. The stabilizing fitting of claim 2, wherein the attaching means includes a VELCRO fastener secured to the upper surfaces of the first and second support members.

10. A stabilizing fitting for an intravenous catheter or syringe, comprising:
    an elongated base having a first support member at a first end thereof, and a second support member at a second end thereof, each of the first and second support members including an upper, generally planar surface having means for attaching the respective support member to a retaining strap;
    a catheter hub/syringe body retainer disposed between the first and second support members;
    a catheter hub/syringe body wing housing centrally disposed between the first and second support members, and surrounding a portion of the catheter hub/syringe body retainer; and
    a plurality of medical tube retaining slots through the base and disposed beneath at least one of the first or second support members.

11. The stabilizing fitting of claim 10, wherein the catheter hub/syringe body retainer includes a frusto-conical first portion extending from one end thereof to a shoulder, a generally cylindrical second portion extending from another end thereof to the shoulder, and a pair of spaced-apart projections extending radially outwardly from the second portion.

12. The stabilizing fitting of claim 10, wherein a longitudinal axis for the catheter hub/syringe body retainer extends generally perpendicular to a longitudinal axis of the base.

13. The stabilizing fitting of claim 12, wherein the medical tube retaining slots run parallel to the longitudinal axis of the catheter hub/syringe body retainer.

14. The stabilizing fitting of claim 13, wherein the attaching means includes a VELCRO fastener.

15. The stabilizing fitting of claim 13, wherein the base has a lower surface including recesses for the catheter hub/syringe body retainer, the wing housing, and the medical tube retaining slots.

16. A stabilizing fitting for an intravenous catheter or syringe, comprising:
    an elongated base having an upper surface, a lower surface, a first support member disposed at a first end thereof, and a second support member disposed at a second end thereof;
    a catheter hub/syringe body retainer centrally disposed between the first and second support members, a longitudinal axis of the catheter hub/syringe body retainer extending generally perpendicular to a longitudinal axis of the base, wherein the catheter hub/syringe body retainer includes a frusto-conical first portion extending from one end thereof to a shoulder, a generally cylindrical second portion extending from another end thereof to the shoulder, and a pair of spaced-apart projections extending radially outwardly from the second portion;

a catheter hub/syringe body wing housing centrally disposed between the first and second support members, and surrounding a portion of the catheter hub/syringe body retainer;

a plurality of medical tube retaining slots through the first and second support members, the medical tube retaining slots running parallel to the longitudinal axis of the catheter hub/syringe body retainer; and means fixed to the upper surface of the base, for attaching the stabilizing fitting to a retaining strap.

17. The stabilizing fitting of claim 16, wherein the attaching means includes a VELCRO fastener secured to the first and second support members.

18. The stabilizing fitting of claim 17, wherein the lower surface of the base includes recesses for the catheter hub/syringe body retainer, the wing housing, and the medical tube retaining slots.

19. A stabilizing fitting for an intravenous catheter or syringe, comprising:

an elongated base having a first support member at a first end thereof, and a second support member at a second end thereof;

a catheter hub/syringe body retainer disposed between the first and second support members; and a medical tube receiving slot through at least one of the first or second support members.

20. The stabilizing fitting of claim 19, including means associated with the first and second support members, for attaching the stabilizing fitting to a retaining strap.

21. The stabilizing fitting of claim 20, wherein a lower surface of the base includes a recess for the medical tube retaining slot.

22. The stabilizing fitting of claim 21, including a plurality of medical tube receiving slots through at least one of the first or second support members, wherein the base lower surface includes a corresponding plurality of recesses for the medical tube receiving slots.

23. The stabilizing fitting of claim 21, including a catheter hub/syringe body wing housing centrally disposed between the first and second support members, and surrounding a portion of the catheter hub/syringe body retainer.

24. The stabilizing fitting of claim 23, wherein the lower surface of the base includes a recess for the catheter hub/syringe body retainer which extends generally perpendicular to a longitudinal axis of the base, and wherein the catheter hub/syringe body retainer includes a frusto-conical first portion extending from one end thereof to a shoulder, a generally cylindrical second portion extending from another end thereof to the shoulder, and a pair of spaced-apart projections extending radially outwardly from the second portion.

25. The stabilizing fitting of claim 24, wherein the attaching means includes a VELCRO fastener secured to the upper surfaces of the first and second support members.

* * * * *